(12) United States Patent
Pallardy et al.

(10) Patent No.: US 6,713,261 B1
(45) Date of Patent: Mar. 30, 2004

(54) METHOD FOR ASSESSING GENOTOXICITY OF A COMPOUND

(75) Inventors: Marc Pallardy, Meudon (FR); Daniel Marzin, Saint Andre (FR); Sophie Meintieres, Lille (FR); Armelle Biola, Moulineaux (FR)

(73) Assignees: Institut National de la Sante et de la Recherche Medicale, Paris (FR); Institut Pasteur de Lille, Lille (FR)

( * ) Notice: Subject to any disclaimer, the term of this patent is extended or adjusted under 35 U.S.C. 154(b) by 0 days.

(21) Appl. No.: 10/130,136

(22) PCT Filed: Nov. 17, 2000

(86) PCT No.: PCT/FR00/03206

§ 371 (c)(1),
(2), (4) Date: Aug. 7, 2002

(87) PCT Pub. No.: WO01/36970

PCT Pub. Date: May 25, 2001

(30) Foreign Application Priority Data

Nov. 19, 1999 (FR) .............................. 99 14603

(51) Int. Cl.$^7$ .......................... C12Q 1/68; C12N 15/00; C12N 15/01; C12N 15/63; C07H 21/04

(52) U.S. Cl. .................... 435/6; 435/440; 435/441; 435/455; 435/325; 435/320.1; 435/69.1; 536/23.1

(58) Field of Search ............................ 435/6, 440, 441, 435/455, 325, 320.1, 69.1, 29; 536/23.1; 436/63, 164, 172, 174, 519, 800

(56) References Cited

PUBLICATIONS

Hilbi et al. Shigella–induced Apoptosis is Dependent in Caspase–1 Which Binds to IpaB. Journal of Biological Chemistry (1998) Vol 273 pp32895–32900.*

Grandgirard et al. Alphaviruses induce apoptosis in Bcl–2 overexpressing cells: evidence for a caspase–mediated proteolytic inacitvatin of Bcl–2. EMBO Journal (1998) Vol 17 pp 1268–1278.*

An et al. Novel dipeptidyl proteasome inhibitors overcome Bcl–2 protective function and selectively accumulate the cyclin–dependent kinase inhibitor p27 and induce apoptosis in transformed but not normal human fibroblasts. (1998) 5 pp 1062–1075 Abstract.*

* cited by examiner

Primary Examiner—Gerry Leffers
Assistant Examiner—Maria Marvich
(74) Attorney, Agent, or Firm—Larson & Taylor PLC

(57) ABSTRACT

The invention concerns a method for assessing in vitro the genotoxicity of a compound, which consist in contacting said compound with at least a cell or cell type overexpressing bcl2 protooncogene and/or related anti-apoptotic protein, and observing the genotoxic effects of said compound on said cell.

8 Claims, 7 Drawing Sheets

METHOD FOR ASSESSING GENOTOXICITY OF A COMPOUND

The invention relates to a method for assessing the genotoxicity of a compound liable to represent a risk to humans or animals.

At a time when combinatorial chemistry is developing, enabling the synthesis of countless novel compounds, short-term toxicological studies are occupying an increasingly important place in the context of the first steps of the development of these compounds, liable to be of value in industries such as the pharmaceutical, agronomic, food and cosmetics industries, etc.

Specifically, the development of a novel compound involves studies which are essential before the very first human exposure and which constitute the "prerequisites". These at least involve studies of toxicity by single and subacute administration and basal assessment of the mutagenic and genotoxic potential.

Since most carcinogenic substances are mutagenic, and vice versa, it is essential for genetic toxicology to use reliable tests which make it possible to come to safe conclusions regarding the potentially mutagenic effects of a compound, by gene mutations, chromosomal mutations or genomic mutations in somatic or germinal cells.

In order to assess the genotoxicity of the compounds of interest, industry makes use of tests which make it possible to demonstrate a clastogenic effect (breaking of chromosomes) or an aneugenic effect (spindle abnormality).

However, the authors of the present invention have shown that the demonstration of a clastogenic effect may be disturbed by compounds which are not clastogenic but which induce apoptosis with the presence of nuclear events. These tested compounds therefore emerge as "false-positives" or "exaggerated-positives" and are ruled out of any subsequent use.

The authors of the present invention have developed a method for assessing the genotoxicity of a compound, which makes it possible to be rid of this problem of "false-positives" or "exaggerated-positives".

More precisely, a subject of the invention is a method for assessing the genotoxicity of a compound, in vitro, in which said compound is brought into contact with at least one cell or cell type overexpressing the bcl2 proto-oncogene and/or a related anti-apoptotic protein, and the genotoxic effects of said compound on said cell are observed.

In other words, a subject of the invention is the use of cells overexpressing the bcl2 proto-oncogene and/or a related anti-apoptotic protein, for assessing the genotoxicity of a compound by being free of the effects linked to apoptosis alone.

The compound to be tested may be any compound of natural or synthetic origin, which is designated indifferently "compound", "product" or "substance". It may be a mixture of several molecules, which may or may not be identified, such as, for example, an extract of animal or plant origin. The compound to be tested may be of therapeutic value, or may be useful in the chemical, agrochemical, food or cosmetics industry in particular.

According to a first embodiment of the invention, these positive genotoxic effects may be observed by the formation of a micronucleus or micronuclei.

This micronucleus test, described in particular by Matsuoka et al., 1993 and Kirsch-Volders et al., 1997, is based on the following principle:

During mammalian cell mitosis, chromosome fragments or whole chromosomes which have not undergone segregation will not be located in the main nucleus during telophase and may be observed, under the microscope, in the form of micronuclei separated from the main nucleus.

The DNA fragments which give rise to the micronuclei may be caused by either lesions to DNA (clastogenic or aneugenic effects of genotoxic compounds) or cleavage subsequent to apoptosis (effects of pro-apoptotic compounds).

According to a second embodiment of the invention, positive genotoxic effects of a compound may be observed by the presence of abnormalities of number and/or of structure of the chromosomes in metaphase.

This metaphase analysis test has, in particular, been described by Evans et al., 1987.

The principle of this test is as follows: the cells are treated with the compound to be tested, and then, by taking out and staining the cells blocked in metaphase (with a blocking agent such as colcemid), chromosomal abnormalities (breaks, rearrangements, etc.) are sought.

These two embodiments (micronucleus test and analytical test in metaphase) may advantageously be carried out in a complementary fashion.

They do not exclude other embodiments of the method of the invention, using cells overexpressing bcl2 and/or a related anti-apoptotic protein.

Moreover, since some compounds require metabolic activation in order to exert their genotoxic effects, it is possible to add, to the compound to be tested, a metabolic activator or activation system, such as "S9 mix", containing a subcellular microsomal fraction of rat liver (Kirkland et al., 1989), in the method of the invention.

In accordance with the present invention, the compound to be tested is brought into contact with cells overexpressing the bcl2 proto-oncogene and/or a related anti-apoptotic protein. The overexpression of bcl2, known to be an inhibitor of apoptosis, creates an imbalance between inducers and inhibitors of apoptosis of the bcl2/bax family. The overexpression of the bcl2 protein thus prevents the cells from undergoing apoptosis.

The expression "bcl2-related anti-apoptotic protein" is intended to mean any protein of the bcl2 family which has anti-apoptotic activity, the characteristics of this family being described by Biolo et al., 1999.

The homology between the various proteins of this family is concentrated in three regions, named BH1, BH2 and BH3, which control their abilities to dimerize with other members of the same family and also their apoptosis-regulating functions. All the anti-apoptotic members also contain a BH4 domain located close to their N-terminal end. These proteins also have, at their C-terminal end, hydrophobic amino acids which appear to be important for anchoring them in intracellular membranes.

Among the bcl2-related anti-apoptotic proteins, mention may preferentially be made of bcl-XL, which exhibits very strong homology with bcl2 (Biolo et al., 1999; Chao et al., 1995).

The cells used are eukaryotic cells, and preferentially mammalian cells. According to a preferred embodiment of the invention, they are CTLL-2 cells. CTLL-2 cells, which are well known to those skilled in the art, originate from a continuous line of cytotoxic T lymphocytes which is a subclone derived from the C57bl/6 mouse. This line is available at the American Type Culture Collection under the number ATCC TIB-214 and has been described in a certain number of publications (Gillis et al., 1997; Hu et al., 1997). Other cell types may also be used, such as, for example, L5178Y, CHO, V79, fibroblasts or human or animal lymphoma cells, or other eukaryotic cells. A CTLL-2 line can be transfected with a plasmid containing bcl2 or a related sequence, according to standard transfection and transformation methods known to those skilled in the art. The preparing of CTLL-2-bcl2 cells has been described, in particular, in the article by Deng et al., 1993.

In accordance with the present invention, the cells may be transfected so as to overexpress a bcl2-related anti-apoptotic protein, such as bcl-XL, according to standard methods within the scope of those skilled in the art who are aware of the sequences of the corresponding genes (Bolse et al., 1993).

The method in accordance with the invention is efficient for detecting false-positives due to the apoptotic phenomenon. In addition, the method makes it possible to detect products which have a true clastogenic or aneugenic capacity without being an inducer of apoptosis.

Sensitivity and Reproducibility of the present method make it a valid method for assessing the genotoxicity of compounds on a large scale.

The following figures and examples illustrate the invention without limiting the scope thereof.

BRIEF DESCRIPTION OF THE DRAWINGS

In all the figures, the stars represented have the following meaning.

*: $p<0.05$ against the negative control
**: $p<0.01$ against the negative control

EXAMPLES

Example 1

Figure 1A:
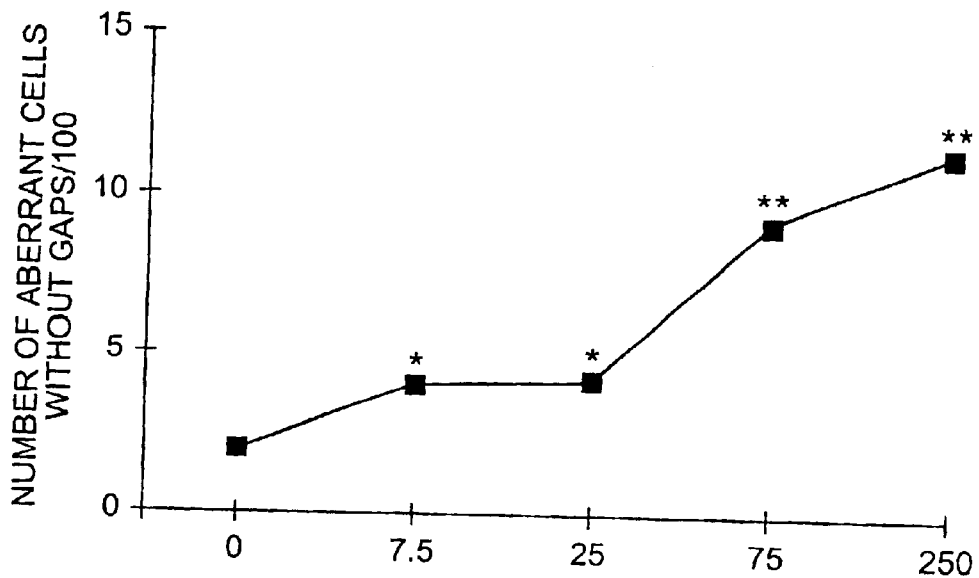
FIG. 1A is a graph which represents an analysis of the metaphases of human lymphocytes treated with dexamethasone for 44 hours.

Micronucleus Test in CTLL-2 and CTLL-2-bcl2 Cells

A—Cell Systems

1) CTLL-2 lymphocytic Cells

The CTLL-2 murine line is a subclone of cytotoxic T lymphocytes derived from the C57bl/6 mouse, the proliferation of which is dependent on recombinant human interleukin-2 (IL-2).

The cells are cultured in a complete RPMI 1640 medium C1 (Gibco BRL), with:

10% of fetal calf serum decomplemented for 30 minutes at 56° C. (Gibco BRL)

0.01% of 20 mg/ml sodium pyruvate (Sigma)

2 mM of L-glutamine (Gibco BRL)

22 mM of HEPES (Sigma)

100 IU/ml of penicillin (Gibco BRL)

0.1 mg/ml of streptomycin (Gibco BRL)

$5 \times 10^{-5}$ M of β-mercapto ethanol (Merck)

1 ng/ml of IL-2

The protocols for freezing, thawing and maintaining the cells at 37° C. are as follows:

freezing of CTLL-2 and CTLL-2 Bcl2 cells

The cells are centrifuged for 5 minutes at 200 g and the pellet is adjusted to $3.5 \times 10^6$ cells per 0.5 ml of decomplemented fetal calf serum, and then 0.5 ml of the cell suspension is transferred into a cryotube containing 0.4 ml of decomplemented fetal calf serum and 0.1 ml of DMSO (Merck; batch K2308267-651), at $3.5 \times 10^6$ cells/ml.

The cells are gradually frozen (−1° C. per minute) and stored in liquid nitrogen at −196° C.

thawing of CTLL-2 and CTLL-2 Bcl2 cells

The cryotube is placed in a water bath at 37° C.

The content is transferred into 49 ml of complete RPMI 1640 medium C1 and then diluted to ¹⁄₁₀th in C1 medium.

After 24 hours in an incubator at 37° C. under an atmosphere at 5% $CO_2$ and 95% humidity, in a 50 ml flask (Falcon, Becton Dickinson), the culture is centrifuged for 5 minutes at 200 g and the pellet is resuspended in 50 ml of C1 and conditioned in 10 ml flasks.

maintaining of CTLL-2 and CTLL-2 Bcl2 cells

The CTLL-2 cells are cultured in C1 medium which is renewed twice a week. The cells, which are counted in Malassez chambers, are diluted such that, at the following passage, the density does not exceed 300 000 cells/ml, given that the doubling time is 12 hours.

The cultures are placed in an incubator at 37° C. under an atmosphere at 5% $CO_2$ and 95% humidity.

2) CTLL-2-bcl2 Cells

The CTLL-2-bcl2 cells are derived from the transfection, by electroporation, of CTLL-2 cells with the plasmid pSFFV-bcl2-neo (plasmid provided by the laboratory of Dr. Korsmeyer, Washington University, Saint Louis, Mo., plasmid reference: 3088) containing a 1.9 kb Eco-RI insert encoding the human bcl2 protein placed under the control of the LTR region of the SV40 virus, and also a gene for resistance to ampicillin and to geneticin (G418) (Renvoizé et al., 1997).

The plasmid is linearized with the ScaI restriction enzyme, in a proportion of 1 unit per cleavage site per µg of plasmid, at 37° C. for 16 hours. The enzyme is then inactivated at 60° C. for 15 minutes and the plasmid is precipitated in 100% ethanol. The cells are transfected with the plasmid (10 µg of plasmid per 10 million cells) by electroporation (Biorad, 250 V, 960 µF). The cells are then put back into culture in complete medium for 48 hours, and the stable transfectants are then selected in the presence of 800 µg/ml of geneticin (Gibco) for at least 15 days, and then by IL-2 deprivation for 48 hours. The cells thus selected are cloned by dilution in 96-well plates (Costar), in a proportion of one cell every two wells.

The freezing, thawing and maintaining of the CTLL-2-bcl2 cells are strictly the same as for the CTLL-2 cells.

3) Peripheral Lymphocytes

The samples of human lymphocytes are obtained by isolation on a ficoll gradient (Hypaque 1077; Sigma; batch 077H6024), after two-fold dilution of the peripheral blood in RPMI 1640 (Gibco BRL; batch 3001360) containing 0.08‰ of heparin (Sanofi) for a better yield.

The blood was collected by venous puncture using the vacutainer system on lithium heparin (Becton Dickinson), under sterile conditions, from a healthy volunteer donor who was a nonsmoker, had not received any recent medical treatment or radiation, and had not been affected by any recent viral infection.

The cells are cultured at 37° C. in a complete RPMI 1640 (Gibco BRL) medium C2, with:

20% of fetal calf serum decomplemented for 30 minutes at 56° C. (Gibco BRL)

22 mM of L-glutamine (Gibco BRL)

100 lU/ml of penicillin (Gibco BRL)

0.1 mg/ml of streptomycin (Gibco BRL)

100 IU of heparin

+2 ml of phytohemagglutinin A (Wellcome) per 100 ml of medium.

B—Products Studied

1) Aneugenic Agents griseofulvin

Griseofulvin is an inhibitor of microtubule formation. It is an antimitotic agent: it disturbs the mitotic spindle by virtue of its interaction with proteins associated with the polymerized microtubules. The griseofulvin (Sigma; batch 85H07391) is dissolved at 200 mM in DMSO (dimethyl sulfoxide), aliquoted and stored at −20° C.

taxol

Taxol is an antineoplastic agent with proven clinical effectiveness. This compound has aneugenic effects and is an apoptosis inducer.

The taxol (Sigman; batch 126H1382) is dissolved at 400 nM in DMSO, aliquoted and stored at −20° C.

nocodazole

Nocodazole affects mictrotubules and therefore causes aneuploidy. In addition, like taxol, it causes phosphorylation of bcl2, stopping of the cell cycle in the M phase and apoptosis.

diethylstilbestrol

Diethylstilbestrol (DES) is an estrogen, the pharmacological properties of which have been exploited for the prevention of spontaneous abortions, and which continues to be used in humans in prostate cancer therapy. This compound increases or decreases the transcription of genes regulated by hormones.

It has been reported that DES has carcinogenic actions in humans, in particular after administration during pregnancy, by inducing aneuploidy subsequent to its effect an centromeres and centrioles.

DES also proves to have clastogenic activity after metabolic activation.

diazepam

Like DES, diazepam is an aneugenic agent. This compound is part of the benzodiazepines and has an anxiolytic and anticonvulsive effect.

2) Clastogenic Agents mitomycin C

Mitomycin C is an antibiotic which engenders single-strand cleavages of DNA and breaking of chromosomes. This compound is a possible carcinogen in humans.

Mitomycin C (Ametycine; batch 440) is dissolved at 500 µg/ml in water for injectable preparations, aliquoted and stored at −20° C.

methyl methanesulfonate

Methyl methanesulfonate (MMS) is a monofunctional alkylating agent which acts by destabilizing DNA, leading to the breaking thereof. It is a possible carcinogen in humans.

The MMS (Aldrich; batch 030177) is dissolved at 7 mM in the RPMI aliquoted and stored at −20° C.

etoposide

The planar cyclic central region, flanked by a phenyl group and by a sugar, makes etoposide a nonintercalating, specific and S phase-dependent inhibitor of topoisomerase II.

This ubiquitous enzyme controls the topology of DNA via the relaxing of supercoiled DNA and the catenation and decatenation thereof during replication, transcription and cell division. This enzyme is essential for chromosome segregation, recombination and separation of chromatids. Etoposide blocks the catalytic activity of topoisomerase 11 by stabilizing the DNA-topoisomerase II complex. Thus, this inhibition produces DNA strand cleavages, with sister chromatid exchanges, chromosomal aberrations and chromosome number abnormalites.

It is an apoptosis inducer: etoposide creates breaks in the genetic material and the P53 protein then stops the cell cycle in the G1 phase so as to allow the transcription of DNA repair genes. When the number of breaks is too high, this exceeds the potential of the repair complexes to come to the aid of the genetic material. P53 then intervenes to trigger the programme of cell death. P53-dependent apoptosis is observed.

These properties explain the fact that etoposide is both a clastogenic agent and an apoptosis inducer.

Etoposide (Sigma; batch 57H1159) is dissolved at 20 mM in DMSO, aliquoted and stored at −20° C.

MNNG and MNU

N-Methyl-N'-nitro-N-nitrosoguanidine (MNNG) and N-methyl-N-nitrosourea (MNU) are two alkylating agents which induce DNA lesions of the O6-methylguanine type, which are known to be mutagenic lesions. These compounds produce lethal lesions which are repaired by a mechanism other than that involving alkyltransferase.

genistein

Genistein is an isoflavone which is abundant in soya-derived products. It behaves like both an agonist and an antagonist of estrogen receptors. It also has the effect of inhibiting protein tyrosin kinases (PTKs) and topoisomerases II, and of inducing cellular differentiation and oxidation events. The genistein comes from Sigma and is stored in DMSO at −20° C.

cyclophosohamide

Cyclophosphamide (CPA) is metabolized to a DNA-alkylating intermediate, the effect of which is interference with DNA synthesis and cell division in a phase-independent manner. It is clearly established that, in normal cells of the bone marrow or of the intestinal epithelium, blocking occurs in the G1/S phase so as to repair the lesions or to enter into apoptosis.

3) Apoptosis Inducers dexamethasone

Dexamethasone is a glucocorticoid which induces apoptosis according to two models; the transcriptional model requires activation of cell death genes via the glucocorticoid receptor, and therefore the molecule does not act on the DNA. Apoptosis may occur according to a model of transrepression, in which factors required for cell survival would be repressed.

The dexamethasone (Sigma; batch 116H0427) is dissolved at 150 mM in DMSO, aliquoted and stored at −20° C.

gliotoxin

Gliotoxin is a fungal metabolite which induces apoptosis by creating protein kinase A-dependent hyperphosphorylation on the serine residues of the H3 histones, making the cells sensitive to the effects of nucleases. The gliotoxin comes from Sigma and is stored in DMSO at −20° C.

methional

Methional, which is a metabolite of methionine, is an apoptosis-inducing agent.

C1—Protocol for the Micronucleus Test Without Metabolic Activation

The compounds tested are as follows: griseofluvin, taxol, mitomycin C, MMS, etoposide, dexamethasone, genistein, gliotoxin, methional, nocodazole and DES.

Implementation of the test on CTLL-2 and CTLL-2 Bcl2 cells $2 \times 10^6$ cells are added to 15 ml tubes, each containing 5 ml of complete RPMI 1640 medium supplemented with 25 µg/ml of IL-2. The product to be studied is then added at various concentrations prepared on a 2-fold basis. In parallel, a tube is treated with the solvent of the product to be studied (in the case of DMSO, a final concentration of 0.2% will not be exceeded) and another is treated with a positive reference product (Mitomycin C at 75 ng/ml; Boehringer; batch 1397592137) in aqueous solution. The tubes are screwed shut and gently vortexed, and then placed in an inclined position in an incubator at 37° C. without agitation.

The CTLL-2 cells, which originate from a permanently dividing continuous line, are all targets for the agent studied, and it is therefore not essential to treat them with cytochalasin B (the effect of which is to block cytokinesis). It is not necessary to limit the analysis to binucleated cells. In addition, cytochalasin B is likely to interfere with the clastogenic potential of the products of interest.

The lymphocytes are harvested at the 15th hour after the start of the incubation (1.5 cell cycles). The cells are washed twice with 5 ml of RPMI 1640 supplemented with 2% of decomplemented fetal calf serum. The cells are then harvested by centrifugation for 5 minutes at 200 g, and then subjected to a hypotonic shock for 8 minutes (1 volume of RPMI 1640:4 volumes of water for injectable preparations +2% of decomplemented fetal calf serum). After centrifugation, as much supernatant as possible is removed and the cells are fixed with 10 ml of Carnoy's fixative mixture II (3 volumes ethanol:1 volume acetic acid) for 10 minutes.

After a further centrifugation, the cells are plated out onto slides and left to dry for 24 hours in the open air, and then stained for 10 minutes with Giemsa reagent diluted to 5% in water.

The cells are then examined microscopically at 1250× magnification and the micronuclei present in the mononucleated cells are sought.

Implementation of the test on peripheral lymphocytes

In the case of lymphocytes, division is induced with phytohemagglutinin A. Given that only the T lymphocytes divide, it is essential to add cytochalasine B in order to examine only the binucleated cells which have undergone mitosis, when searching for micronuclei.

Cells which have undergone 20 hours of preculturing in C2 complete medium supplemented with phytohemagglutinin A (Murex Biotech; batch F067610) are brought into the presence of the product to be studied.

At the 44th hour after the start of the incubation, the circulating lymphocytes are washed twice with culture medium containing 10% of dfcs in order to remove the product, and then complete medium containing cytochalasin B (Sigma; batch 87H4054) is added, at a final concentration of 6 µg/ml.

At the 68th hour after the start of the incubation, the lymphocytes are harvested and undergo the same treatment as above. On the other hand, the micronuclei are sought only in the binucleated cells.

C2—Protocol for the Micronucleus Test With Metabolic Activation

Some products require metabolic activation in order to exert their genotoxic effects. In vitro, this activation is carried out using the S9 Mix. S9 is a subcellular microsomal fraction of liver from rats induced with Aroclor. The composition of the S9 mix (Kirkland et al., 1989) is as follows:

2 ml S9 (prepared in the laboratory)

1 ml KCl at 150 g/l 1 ml glucose-6-phosphate at 180 g/l 1 ml NADP at 25 g/l

This assay is intended to determine whether there is a response, in terms of genotoxicity or of apoptosis, subsequent to the metabolic activation of a compound by the S9 Mix.

$0.5 \times 10^6$ cells are added to 15 ml tubes, each containing complete RPMI 1640 medium supplemented with interleukin 2 at a final concentration of 25 µg/ml. The final volume is 5 ml.

0.25 ml of S9 Mix and the product to be tested are added. In this example, this product is cyclophosphamide (CPA).

In parallel, a tube is treated with the solvent of the product.

Incubation is then carried out in a water bath at 37° C. for 3 hours with agitation at low speed (B.M. GYROTORY G76: set at 2.5, i.e. approximately 80 cycles per minute).

At the end of this period of time, the mixture is centrifuged and the supernatant is removed.

Washing is then carried out twice with 5 ml of RPMI containing 10% of decomplemented fetal calf serum.

The mixture is centrifuged and the supernatant is removed down to approximately the 0.5 ml mark, and 4.5 ml of complete RPMI medium supplemented with 25 µg/ml of interleukin 2 are added.

The mixture is returned to the incubator for a further 15 hours.

Harvesting is carried out according to the same procedure as in the micronucleus test without metabolic activation.

D—Measurement of Apoptosis

1) Detection of Apoptosis With Annexin V-FITC (Euromedex)

The cells treated in parallel to the mutagenesis techniques are washed in culture medium in order to remove the product and are suspended in HEPES/NaOH buffer (10 mM HEPES; pH 7.4; 140 mM NaCl; 5 mM KCl; 5 mM CaCl$_2$) at $10^6$ cells/ml.

100 μl of this suspension are brought into the presence of 90 μl of Annexin V-FITC (diluted at 10 μg/ml in HEPES buffer) for 15 minutes in the dark at laboratory temperature. Finally, 10 μl of propidium iodide diluted in HEPES buffer, at the concentration of 50 μg/ml, are added.

Flow cytometry analysis is performed on Epics Profile (Coulter Coultronic, Margency): the level of fluorescence emitted by the Annexin-V-labeled cells is determined after it has passed through a filter at 525±10 nm and displayed after logarithmic amplification. The fluorescence emitted by the propidium iodide is measured at 600 nm.

2) Detection of apoptosis with YOPRO-1 (Molecular Probes, Eugene, Oreg.) The cells treated in parallel to the mutagenesis techniques are washed in culture medium in order to remove the product.

The diluted YOPRO-1 (1V YOPRO-1:100V EPPI) is added in a proportion of 1 μl/0.5×$10^6$ cells suspended in 0.5 ml of RPMI 1640.

Flow cytometry analysis is performed on Epics Profile (Coulter Coultronic, Margency): the level of fluorescence emitted by the YOPRO-1-labeled cells is determined after it has passed through a 525±10 nm filter and displayed after logarithmic amplification.

E—Expression of the Results

The results obtained at the end of the search for micronuclei and of the induction of apoptosis are studied using the $\chi^2$ test, by statistical comparison of the results with those obtained with the solvent control, this being for the preliminary studies.

For the search for micronuclei in triplicate and the study of apoptosis in duplicate, the authors of the invention performed a single-factor analysis of variance. In the event of significance, the Dunnett's test for multiple comparison was performed.

Using analysis of variance for regression, the authors of the invention verified that a significant correlation exists between the number of micronuclei observed or the percentage of apoptotic cells and the concentration of product.

F—Results

1) Overexpression of the bcl2 Protein Eliminates the False-positives By Apoptosis The authors of the invention have shown that a true correlation exists between the results obtained on the CTLL-2 and CTLL-2-bcl2 murine lines in terms of induction of micronuclei in the case of cells treated with a strictly aneugenic agent (griseofulvin) or clastogenic agents not recognized as being apoptosis inducers (mitomycin C and MMS). Whatever the line, the apoptotic phenomenon is not triggered, whereas the micronucleated cell frequencies increase significantly with the dose. In addition, the amplitude of the clastogenic and aneugenic manifestations is comparable in the two lines.

Moreover, in order to prove that the apoptotic effect is added to the genotoxic effect, the lines were treated with aneugenic or clastogenic agents which are also apoptosis inducers: taxol and etoposide, respectively. It is effectively shown that the CTLL-2-bcl2 model makes it possible to distinguish between the effects due to apoptosis and those due to clastogenesis or to aneugenesis. Since the cells transfected with the gene encoding the bcl2 protein have the property of not being sensitive to apoptotic agents due to the imbalance artificially created between the members of the bcl2 family, the high concentration of the protein is always greater than that of the apoptosis-inducing proteins.

Figure 6A:
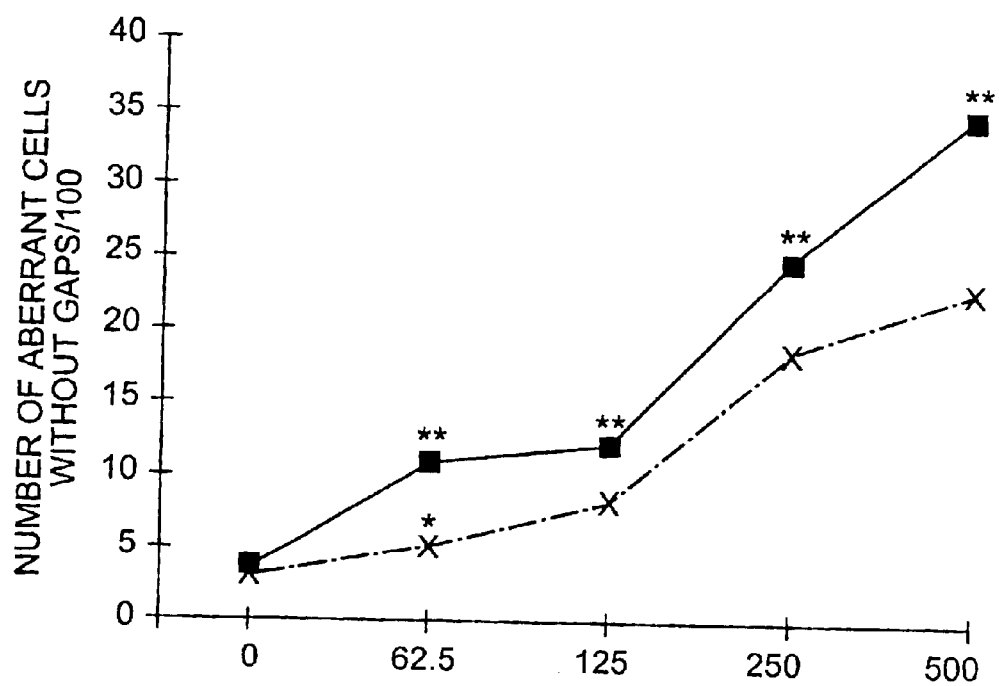
FIG. 6A represents the number of micronucleated cells among the CTLL-2 cells (solid line) and CTLL-2-bcl2 cells (broken line) treated with etoposide.
Figure 6B:
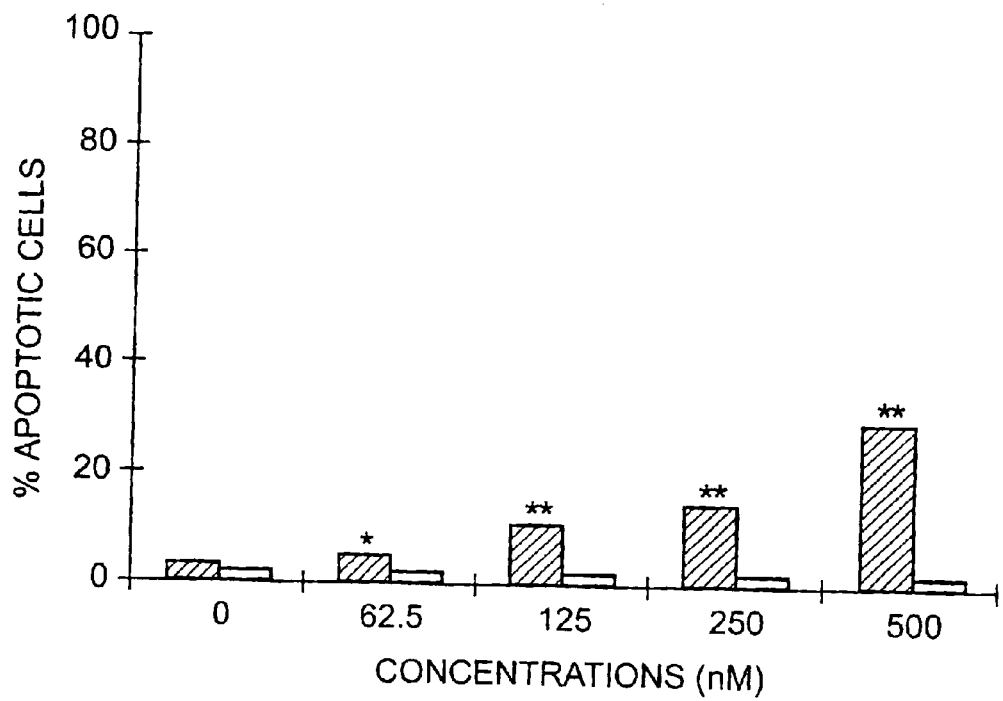
FIG. 6B represents the measurement of apoptosis in the CTLL-2 cells (hatched columns) and CTLL-2-bcl2 cells (white columns) treated with etoposide, according to the Annexin-V-FITC detection method.

Although they act via different mechanisms of apoptosis induction, the two agents engender comparable phenomena: both induce apoptosis and also the formation of micronuclei in the CTLL-2 cells. On the other hand, in the CTLL-2-bcl2cells, there is much less formation of micronuclei. The difference in evolution of the number of micronuclei between the CTLL-2 line and the CTLL-2-bcl2 line already appears at the first concentration of taxol (25 nM). Similarly, it occurs at the first dose of etoposide (62.5 nM; FIGS. 6A and 6B).

On the other hand, the line transfected with the gene encoding the apoptosis-inhibiting bcl2 protein reflects the genotoxic effect of the agents studied by eliminating the apoptotic component. Thus, observation of the evolution of the number of micronuclei in FIG. 6A, which shows different slopes in the CTLL-2 and CTLL-2-bcl2 lines, shows that part of the induction of the micronuclei by etoposide is due to the apoptotic phenomenon and that part is due to the clastogenic effect per se of the compound.

Figure 3A:
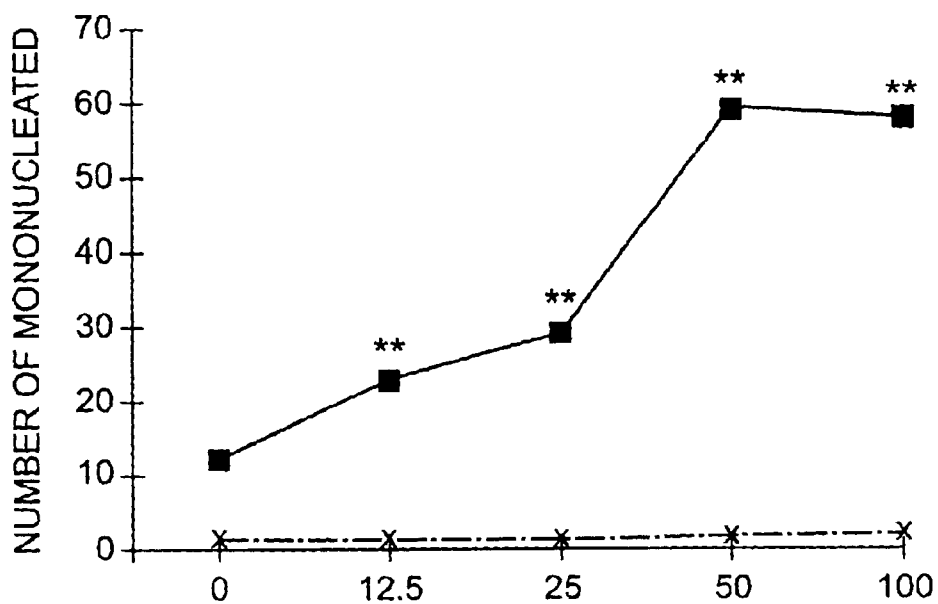
FIG. 3A represents the number of micronucleated cells among the CTLL-2 cells (solid line) and CTLL-2-bcl2 cells (broken line) treated with dexamethasone.
Figure 3B:
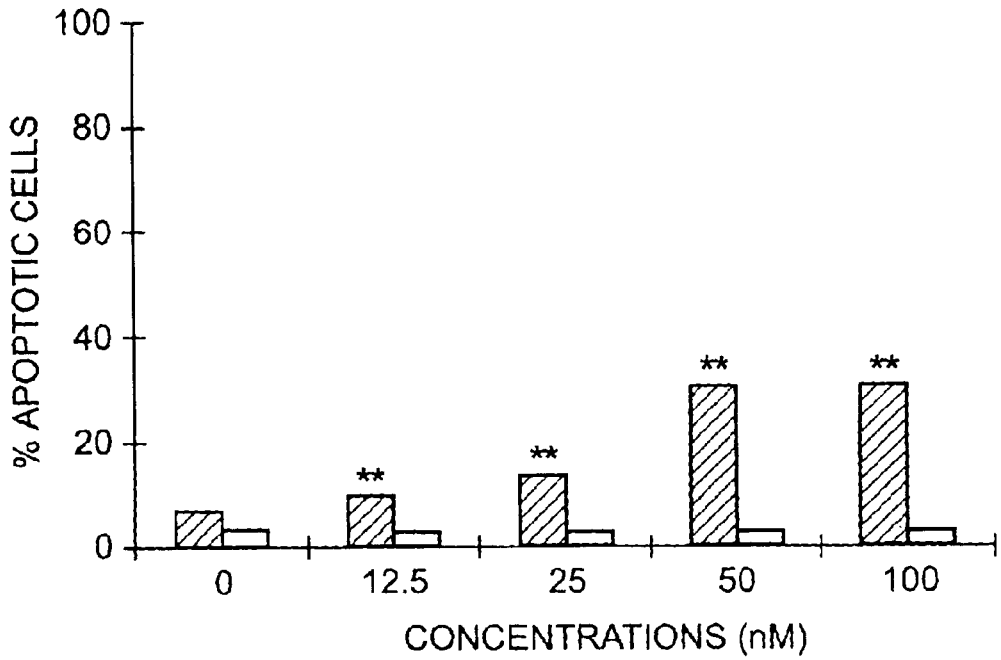
FIG. 3B represents the measurement of apoptosis in the CTLL-2 cells (hatched columns) and CTLL-2-bcl2 cells (white columns) treated with dexamethasone, according to the Annexin-V-FITC detection method.

The authors of the invention induced the formation of micronuclei and apoptosis only in the CTLL-2 cells at doses between 12.5 nM and 100 nM of dexamethasone (FIGS. 3A and 3B).

In this model, the percentage of micronucleated cells, which was 3‰ in the negative control, increased to give a maximum of 60‰ from 50 nM of dexamethasone.

Such results would make it possible to conclude that the dexamethasone had mutagenic properties, but the number of cells with micronuclei increased in similar fashion to the increase in the percentage of apoptotic cells. The latter increased from 6% (in the negative control) to 30.5% according to the methods with Annexin-V-FITC and YOPRO-1, and a maximum was also observed from 50 nM of dexamethasone.

Whatever the dexamethasone concentrations, it was not possible to observe either an increase in apoptotic cells or an increase in micronucleated cells in the CTLL-2-bcl2 strain, again suggesting that the apoptosis is responsible for the false-positive results.

The studies on dexamethasone, an acknowledged inducer of apoptosis in lymphocytic cells, therefore make it possible to demonstrate the value of the CTLL-2-bcl2 model in distinguishing a genotoxic product from an apoptotic product. It does not allow any induction of apoptosis to appear, nor any formation of micronuclei, whereas the nontransfected CTLL-2 line underwent the apoptotic phenomenon, which is accompanied by an increase in aberrant cell rate. By the same token, this shows that the source of the micronuclei is the DNA fragments formed by endonucleases activated during the process of apoptosis. These apoptosis-derived fragments can be revealed by a characteristic "ladder" image after agarose gel electrophoresis.

The CTLL-2/CTLL-2-bc2 Model Detects Genotoxic Products

In the in vitro micronucleus test, a product is classified as genotoxic if it causes a statistically significant and dose-dependent increase in the frequency of micronuclei, relative to the negative control.

At the end of the treatments with the purely clastogenic and purely aneugenic agents (mitomycin C, MMS, griseofulvin), it was possible to note, in each of the two cell lines, not only a statistically significant increase in the frequency of aberrations, but also a dose-dependent increase: the criteria for classifying a product in the genotoxic product category are therefore satisfied. In addition, the two lines have the same sensitivity to the products with which they were brought into contact since, for a given concentration of a product tested, the number of micronucleated cells is comparable in the two lines, without there being any visible apoptosis.

The criteria for positive results are also satisfied in the study of the products which are clastogenic or aneugenic and, at the same time, apoptosis inducers (etoposide and taxol), in the CTLL-2 and CTLL-2-bcl2 lines. However, the latter line also has the property of only revealing the aneugenic and clastogenic role of these two products. Specifically, with regard to etoposide (clastogenic) and taxol (aneugenic), an increase in the incidence of micronuclei is noted outside any apoptotic event. In the case of etoposide, an increase in the frequency of micronuclei in the CTLL-2-bcl2 cells, which do not enter into apoptosis, is observed from 12.5 to 100 nM. With taxol, an increase is observed in the number of micronuclei at 25 nM on CTLL-2 cells and at 50 nM on CTLL-2-bcl2 cells, whereas these doses do not cause apoptosis. These observations show that the CTLL-2-bcl2 line is a good model not only for detecting false-positives due to apoptosis, but that it also allows a compound to be attributed its genotoxic role.

In addition, studying a pure apoptosis inducer such as dexamethasone, makes it is possible to demonstrate the role of apoptosis as a source of false-positives, since its effects on the CTLL-2 line are characteristic of a genotoxic product. However, such a potential can in no way be attributed to the role of apoptosis in the line transfected with the gene encoding the apoptosis inhibitor bcl2.

Figure 4A:
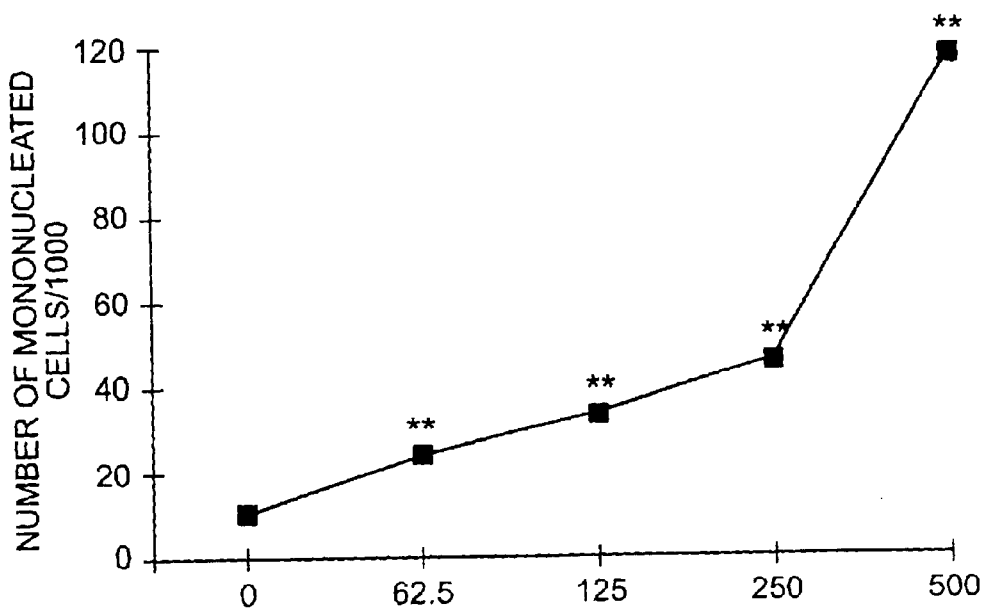
FIG. 4A represents the number of micronucleated cells among the human lymphocytes treated with etoposide for 4 hours.
Figure 4B:
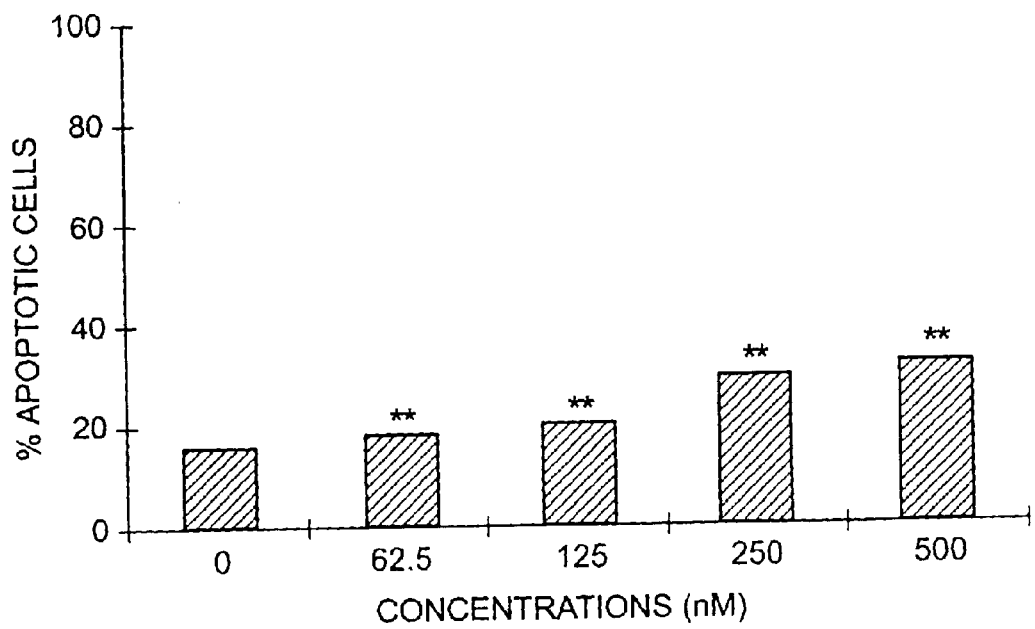
FIG. 4B represents the measurement of apoptosis in the human lymphocytes treated with etoposide, according to the Annexin-V-FITC detection method.

The CTLL-2/CTLL-2-bcl2 Lines Exhibit Good Sensitivity With Respect to the Products Studied The quality of the model developed is confirmed, moreover, by the good sensitivity thereof. It is noted that, for each of the products tested, the responses are comparable between the assays carried out in triplicate and those carried out in screening and those noted with human lymphocytes in culture (cf. FIGS. 4A and 4B on human lymphocytes in comparison with FIGS. 6A and 6B on CTLL-2 and CTLL-2-bcl2). Moreover, it is observed that the results obtained with the true genotoxic agents (mitomycin C, MMS, griseofulvine) are the same in the two lines, which means that the overexpression of bcl2 does not modify the sensitivity of the cells to the aneugenic or clastogenic effect of a product.

Finally, the reproducibility between results obtained in screening and results obtained in the assays in triplicate, and the repeatability of the assays in triplicate, with low standard deviations, make it possible to conclude that the interpretation of the results is of good quality.

By studying gliotoxin or methional, the authors of the invention were, as in the case of dexamethasone, able to demonstrate the fact that the CTLL-2/CTLL-2-bcl2 model makes it possible to conclude that the products inducing only apoptosis were responsible for the formation of micronuclei, leading to a falsely positive conclusion in terms of genotoxicity.

As in the case of the study with dexamethasone, in the CTLL-2 cells treated with methional at doses ranging from 60.8 $\mu$M to 150 $\mu$M, induction of apoptosis and formation of micronuclei was observed within the same period of time. The level of apoptotic cells reached 24% at the highest dose, against 6.5% in the control, whereas the number of micronucleated cells increased to 98‰, against 11‰ in the control. In the determination of micronucleated cells, as in the induction of apoptosis, the results were statistically significant (p=0.01) from the first dose of methional (60.8 $\mu$M). Whatever the methional concentration, neither apoptosis nor micronuclei appeared in the cells transfected with bcl2. In this case also, the micronuclei induced in the CTLL-2 cells were due to apoptosis.

Gliotoxin was also studied at doses ranging from 25 nM to 200 nM in the model developed. While apoptosis was maintained at a lower rate in the CTLL-2-bcl2 cells, as was the number of micronucleated cells in the nontransfected cells, the level of apoptosis increased from 7.5% to 45% at the highest dose and the number of aberrant cells increased from 5‰ to 20‰. In the micronucleus test and in the apoptosis test, the results are different from the control (p=0.01) from 100 nM.

Additional results

Nocodazole, genistein, camptothecin, brefeldin A, anisomycin C, curcumin, quinacrin and thapsigargine induce apoptosis via different mechanisms in the CTLL-2 line.

As in the case of etoposide, an exaggerated response in terms of mutagenesis is observed in the CTLL-2 line by the appearance of apoptosis at the high concentrations of products, whereas the magnitude of the number of micronucleated cells is less in the CTLL-2-bcl2 line.

The CTLL-2/CTLL-2 Bcl2 model makes it possible to differentiate the apoptotic effect from the mutagenic effect when reading the results of the micronucleus test on CTLL-2.

MNU, diazepam and ethyl methanesulfonate (EMS) cause a positive response in the micronucleus test on CTLL-2 and CTLL-2-bcl2, with the same amplitude in each of the two lines without inducing apoptosis, confirming the fact that this model makes it possible to detect products having genotoxic capacities, whether or not the products are apoptosis inducers.

Actinomycin D and staurosporine, as in the case of dexamethasone, for example, induce a positive response in terms of clastogenesis in the CTLL-2 cells, correlated with the induction of apoptosis. In the CTLL-2-bcl2 cells, neither apoptosis nor genotoxicity is observed, demonstrating the efficiency of the model in eliminating the interference due to apoptosis in the in vitro micronucleus test.

Results with metabolic activation:

After metabolic activation, cyclophosphamide (CPA), benzo[a]pyrene and 7,12-dimethylbenz[a]anthracene (DMBA) induce the formation of micronuclei on the CTLL-2 and CTLL-2-bcl2 cells, and also apoptosis only on the CTLL-2 cells, showing that the cells are capable of providing a response in terms of mutagenesis and of apoptosis subsequent to the treatment thereof with a direct mutagen.

Example II

Metaphase Analysis Test in CTLL-2 and CTLL-2-bcl2 Cells

A—Materials

The cell systems are the same as in Example I (micronucleus test).

B—Principle

The murine cells are treated with the product to be studied, and then, by plating out and staining the cells blocked in metaphase with colcemid, abnormalities of chromosomal number and structure are sought.

Annexin-V-FITC is the technique selected to determine the percentage of cells in apoptosis.

The concentrations selected correspond to the doses used in the in vitro micronucleus test in these cells.

C—Protocol $1 \times 10^6$ cells are added to 15 ml tubes, each containing complete RPMI 1640 medium.

The product to be studied is then added at various concentrations, the final volume having to be 10 ml.

In parallel, a tube is treated with the solvent of the product (in the case of DMSO, a final concentration of 0.2% is not exceeded) and two others are treated with a reference clastogenic product (MMS at 200 µM) and with a reference apoptosis inducer (dexamethasone at 150 nM).

The tubes are screwed shut and gently vortexed, and then placed in an inclined position in an incubator with agitation at 37° C.

The colcemid is added, at the final concentration of 100 ng/ml, at the 13th hour of treatment.

At the 15th hour of treatment, the cells are harvested by centrifugation for 5 minutes at 200 g and subjected to a hypotonic shock (75 mM KCl) for 5 minutes.

After centrifugation, as much supernatant as possible is removed and the cells are fixed with 10 ml of Carnoy's fixative mixture (3V methanol:1V acetic acid) for 10 minutes.

After a further centrifugation, the cells are plated out onto slides and left to dry for 24 hours in the open air, and then stained for 10 minutes with Giemsa's reagent diluted to 4% in water.

The slides are examined under a microscope and chromosomal aberrations (breaks, rearrangements, etc.) are sought.

D—Expression of the Results

The results obtained at the end of the metaphase analyses are studied using a Student's t test. Although the standard deviations do not make it possible to demonstrate that the distribution is normal, the test can be used given the size of the sample. The set of numerical aberrations and the set of cell numbers, with or without gaps, are treated from a statistical point of view using the $\chi^2$ test, as is the number of apoptotic cells.

Firstly, the three recognized purely apoptosis inducers, dexamethasone, gliotoxin and methional, were tested in the metaphase analysis test developed in the CTLL-2 and CTLL-2-bcl2 cells with the aim of determining whether the fragmentation which occurs during the apoptotic phenomenon could give rise to the observation of chromosome breaking in the metaphase-arrested treated cells.

Then, the question of whether the transfection of the apoptosis inhibitor makes it possible to observe a lesser frequency of aberrations when the cells are treated with an agent which is both clastogenic and apoptosis-inducing, such as etoposide, was investigated.

E—Results

Figure 1B:
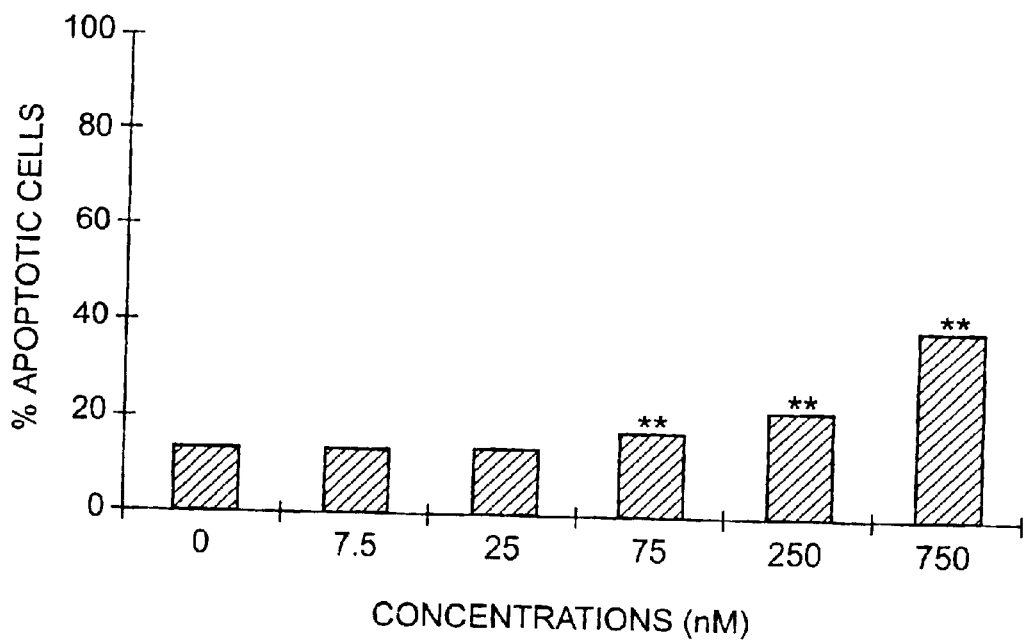
FIG. 1B represents the measurement of apoptosis in the human lymphocytes treated with dexamethasone, according to the Annexin-V-FITC detection method.

In the in vitro metaphase analysis on human lymphocytes, dexamethasone (FIGS. 1A and 1B) may be considered to be a clastogenic agent, although this compound is known to be an apoptosis inducer without being genotoxic.

The lymphocytes were treated for 44 hours with a series of doses of 7.5 µM to 750 µM of dexamethasone, which induced aberrations in a dose-dependent manner. From 250 µM of dexamethasone, apoptosis, which was approximately 16% in the control, increased to 40% of the cells. 11% of aberrant cells were observed against 2% in the control.

Figure 2A:
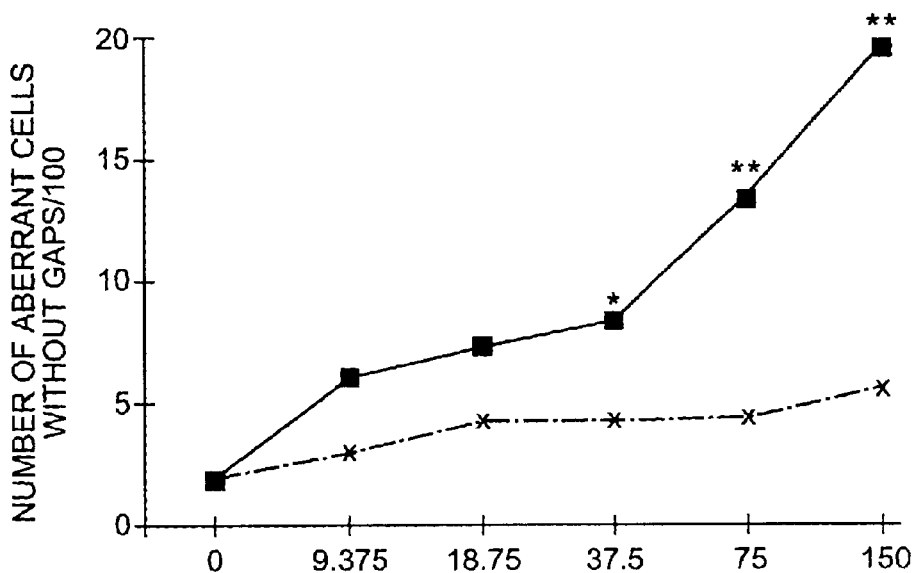
FIG. 2A represents an analysis of the metaphases of CTLL-2 cells (solid line) and CTLL-2-bcl2 cells (broken line) treated with dexamethasone.
Figure 2B:
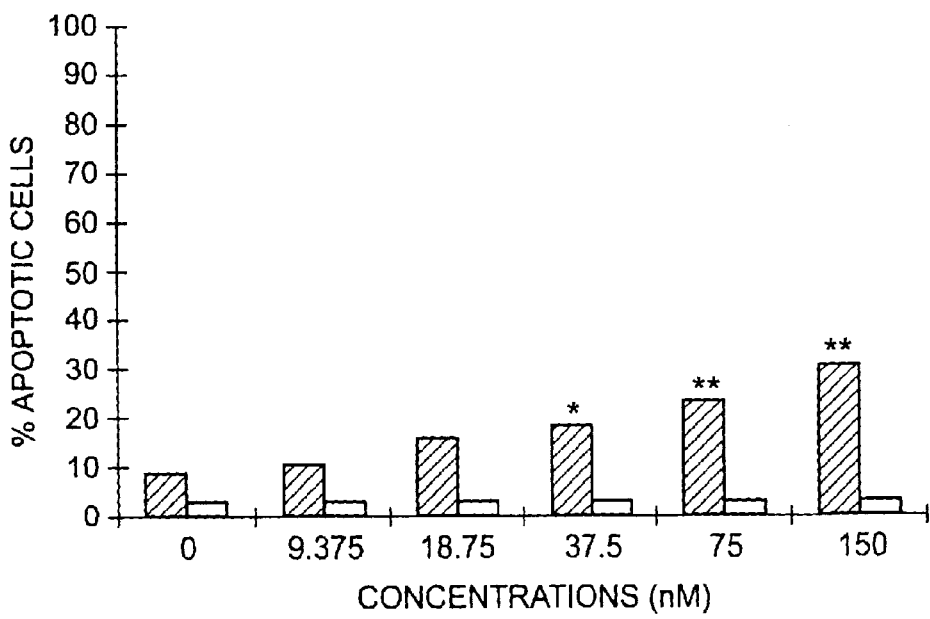
FIG. 2B represents the measurement of apoptosis in the CTLL-2 cells (hatched columns) and CTLL-2-bcl2 cells (white columns) treated with dexamethasone, according to the Annexin-V-FITC detection method.

In order to distinguish the part played by apoptosis in the chromosome and chromatid breaking, the authors of the invention compared the results obtained in CTLL-2 cells transfected with the apoptosis inhibitor bcl2 relative to the results obtained on nontransfected CTLL-2 cells, in an in vitro metaphase analysis, with a dose of between 9.575 nM and 150 nM of dexamethasone (FIGS. 2A and 2B). In parallel, the apoptotic induction was measured. In the CTLL-2 cells, the number of aberrant cells was statistically different (p=0.05) from the control, from 37.5 nM of dexamethasone. 8% of aberrant cells, against 2% in the control, was in fact observed.

As in the human lymphocytes, the authors of the invention observed chromosome and chromatid breaking but no exchange, and within the same period of time, from 37.5 nM of dexamethasone; the apoptosis, which was approximately 7% in the control, increased to 18%, reaching 30% at 150 nM. This demonstrates the function of apoptosis in the DNA fragmentation in the metaphase analysis.

The treatment of two cell lines, in metaphase analysis, with 9.375 µM to 150 µM of methional reveals structural aberrations, such as breaks or gaps, from only the second dose in the nontransfected cells. The difference was statistically significant in comparison with the control (p=0.05), with 13% of cells bearing chromosomal aberrations at 18.75 µM (against 3% in the control).

The metaphase analysis for the cells treated using from 25 to 100 µM of gliotoxin showed a positive response in the CTLL-2 cells, from 50 µM of gliotoxin, in terms of clastogenesis (10% of aberrant cells against 1% in the control), but a large increase in apoptosis is also noted (17% against 5% in the controls). At a higher dose, the metaphases could no longer be analyzed, while the apoptosis reached its maximum. The results and differences observed in the cells containing the apoptosis inhibitor, against those which were not transfected, show that the apoptotic phenomenon leads to "false-positive" results in terms of genotoxicity, as in the micronucleus test.

The in vitro metaphase analysis of the human lymphocytes treated with etoposide reveals a statistically significant increase in the number of aberrant cells, from 125 nM to 500 nM of the compound, with many chromosomal exchanges and complex rearrangements, which is proof of an attempt at DNA repair.

Beyond this concentration, it is not possible to interpret the metaphases because there are too many breaks and rearrangements, and apoptosis appears from 2 000 nM of etoposide, to reach 47% (whereas it was approximately 19% in the control).

Figure 5A:
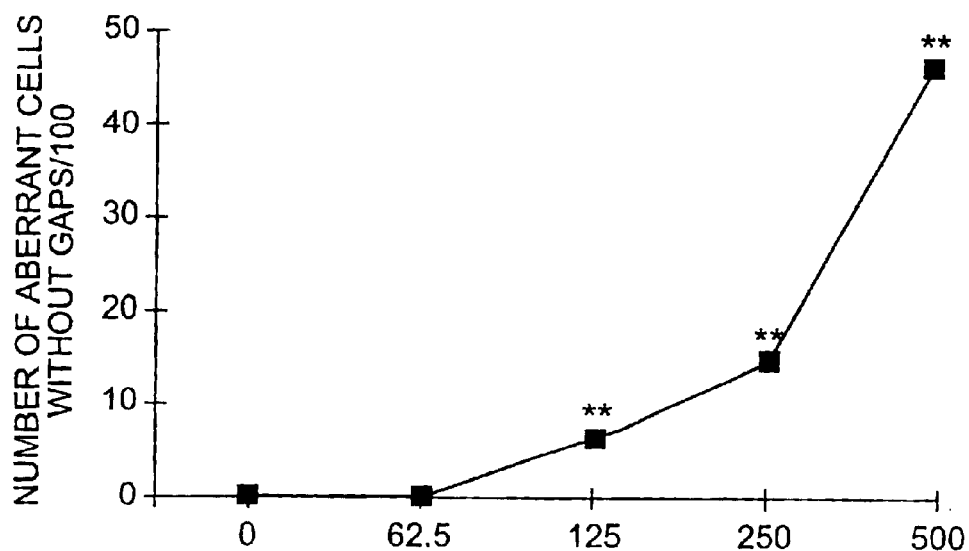
FIG. 5A represents an analysis of the metaphases of human lymphocytes treated with etoposide for 4 hours.
Figure 5B:
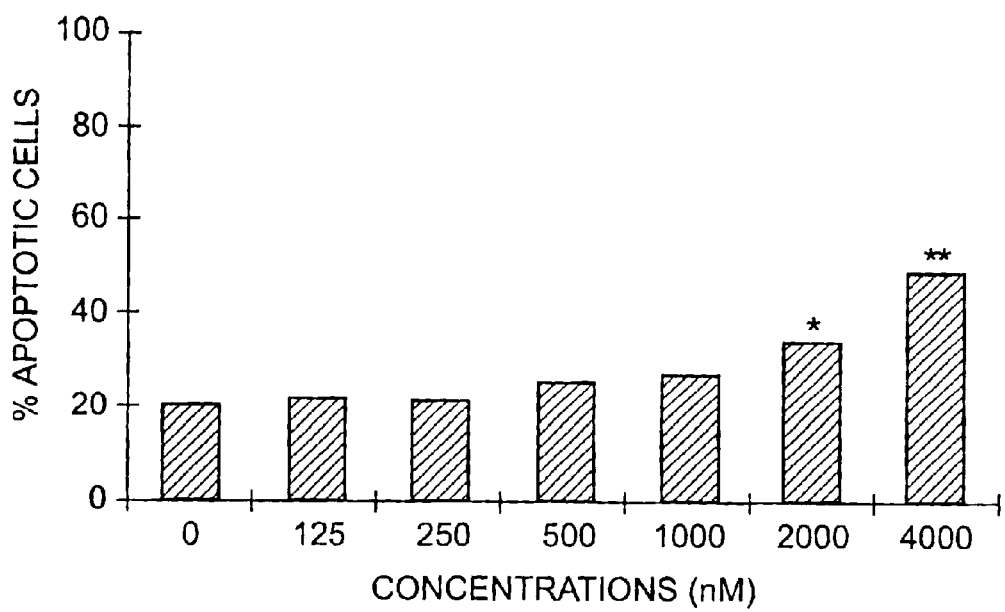
FIG. 5B represents the measurement of apoptosis in the human lymphocytes treated with etoposide, according to the Annexin-V-FITC detection method.

This test makes it possible to describe etoposide as being a genotoxic compound (FIGS. 5A and 5B).

Figure 7A:
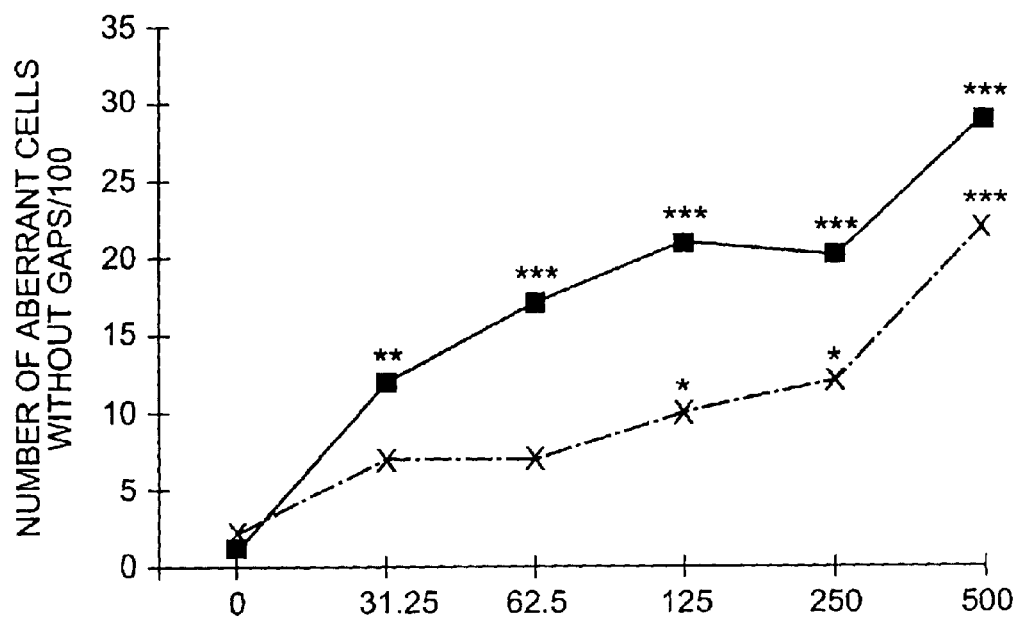
FIG. 7A represents an analysis of the metaphases of the CTLL-2 cells (solid line) and CTLL-2-bcl2 cells (broken line) treated with etoposide.
Figure 7B:
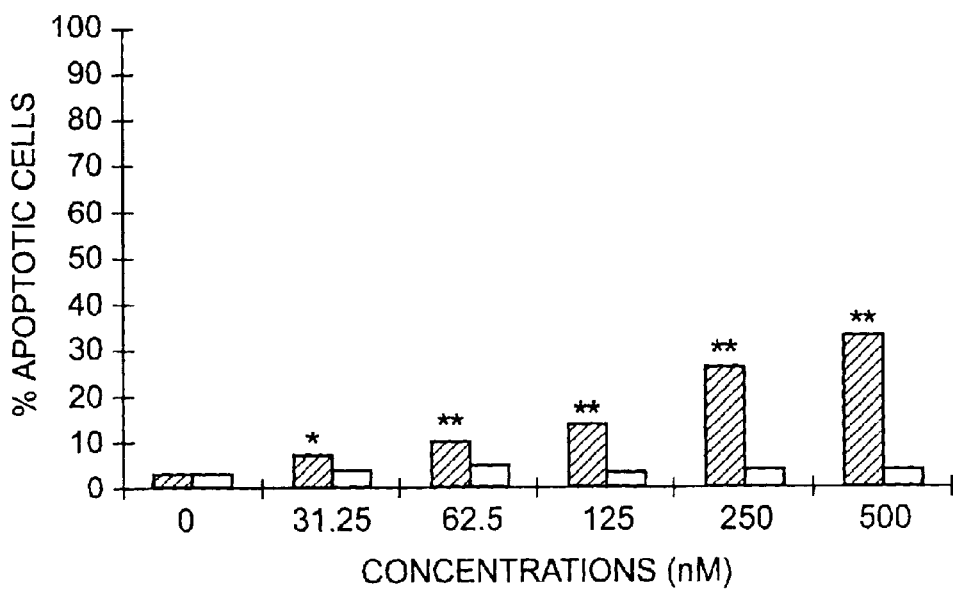
FIG. 7B represents the measurement of apoptosis in the CTLL-2 cells (hatched columns) and CTLL-2-bcl2 cells (white columns) treated with etoposide, according to the Annexin-V-FITC detection method.

In the micronucleus test, the authors of the invention obtained, with high concentrations of etoposide, respectively 4.5‰ (against 2.5‰ in the control) and 29‰ (against 5‰ in the control) of micronucleated cells with complete inhibition of apoptosis. This observation is also valid in the metaphase analysis for CTLL-2 cells treated with 31.25 to 500 nM of etoposide (FIGS. 7A and 7B). The experiment reveals a statistically significant increase (p=0.01) in the number of aberrant cells from 62.5 nM to 500 nM of the compound, with chromosomal exchanges and complex rearrangements, which is proof of an attempt at DNA repair, and the apoptosis also increased significantly from the first dose of etoposide. On the other hand, in the CTLL-2-bcl2 cells, the difference (p=0.05) with the control appeared from 125 nM of the compound, with no apoptosis.

F—Conclusion

As in the micronucleus test, the latter results make it possible to show that apoptosis can engender false-positive results in the metaphase analysis test in CTLL-2 cells as well, whereas transfection with bcl2 eradicates these events.

By virtue of these results, in accordance with those which were observed in the in vitro micronucleus test in the CTL-2/CTLL-2-bcl2 model, a new test is therefore available: the in vitro metaphase analysis test, which detects aberrations of chromosomal or chromatid structure and numerical aberrations.

What is claimed is:

1. A method for assessing genotoxicity of a compound, in vitro, in which said compound is brought into contact with at least one cell overexpressing a bcl2 proto-oncogene and/or a bcl2-related anti-apoptotic protein, and positive genotoxic effects of said compound on said cell are observed as a) formation of a micronucleus or micronuclei or b) presence of abnormalities of number and/or structure of chromosome in metaphase.

2. The method as claimed in claim 1, in which an observation of positive genotoxic effects of the compound are characterized by a formation of a micronucleus or micronuclei.

3. The method as claimed in claim 1, in which positive genotoxic effects of the compound are characterized by a presence of abnormalities of number and/or of structure of chromosomes in metaphase.

4. The method as claimed in claim 1, in which the cell overexpressed bcl2.

5. The method as claimed in claim 1, in which the cell overexpressed bcl-XL.

6. The method as claimed in claim 1, in which the cell is a cell of a CTLL-2 murine line which has been transfected with a nucleic acid expressing bcl2 and/or a bcl2-related anti-apoptotic protein.

7. The method as claimed in claim 1, in which said compound to be tested is in the form of a mixture of molecules.

8. The method as claimed in claim 1, in which a metobolic activator is added to the cell to the compound to be tested.

* * * * *